United States Patent [19]

Helling et al.

[11] Patent Number: 4,943,519
[45] Date of Patent: Jul. 24, 1990

[54] LIGHT SENSITIVE, STABILIZED PHOTOGRAPHIC RECORDING MATERIAL

[75] Inventors: Günter Helling, Odenthal; Johannes Sobel, Leverkusen; Hans Langen, Bonn, all of Fed. Rep. of Germany

[73] Assignee: AGFA-Gevaert Aktiengesellschaft, Leverkusen, Fed. Rep. of Germany

[21] Appl. No.: 816,746

[22] Filed: Jan. 7, 1986

[30] Foreign Application Priority Data

Jan. 19, 1985 [DE] Fed. Rep. of Germany ....... 3501722

[51] Int. Cl.$^5$ ................................................. G03C 1/84
[52] U.S. Cl. .................................... 430/512; 430/517; 430/551; 430/609
[58] Field of Search ................. 430/512, 517, 551, 609

[56] References Cited

U.S. PATENT DOCUMENTS 3,598,600  8/1971  Tuites et al. ........................ 430/609
4,464,463  8/1984  Kojima et al. ..................... 430/551
4,528,264  7/1985  Ishigura et al. ..................... 430/609

Primary Examiner—Jack P. Brammer

[57] ABSTRACT

A photographic recording material contains a stabilizer in polymeric form corresponding to the following formula I

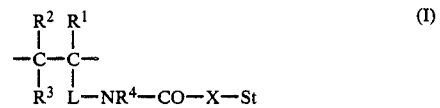

wherein the substituents have the meanings stated in the description.

2 Claims, 1 Drawing Sheet

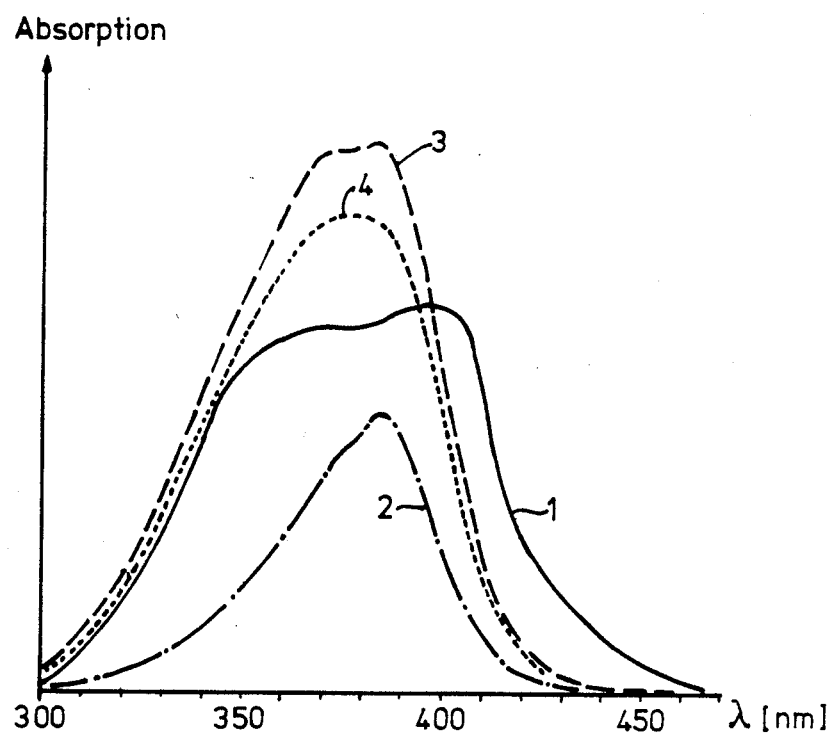

LIGHT SENSITIVE, STABILIZED PHOTOGRAPHIC RECORDING MATERIAL

This invention relates to a photographic recording material having at least one light sensitive silver halide emulsion layer and optionally other layers and at least one stabilizer present in a polymeric form.

It is known to introduce stabilizing additives into silver halide materials to improve the stability. UV absorbers, for example, prevent the undesirable effect of UV light during exposure or as a result of electrostatic charging. Stabilizers may also be used to improve the fastness to visible light. The fog in silver halide materials can be suppressed or reduced by means of so called stabilizers and anti-fogging agents. UV absorbers, light stabilizers and stabilizers and anti-fogging agents for influencing the fog are uniformly distributed in photographic recording materials.

Such stabilizing additives may be introduced into the recording material, for example, in the form of solutions or they may be incorporated in an oil former such as tricresyl phosphate, but considerable disadvantages then arise. Amino allylidene malodinitriles, for example, are known as UV absorbers for photographic recording materials but they teno to form aggregates easily which result in an undesirably broad absorption band with low absorption. The flanks of the absorption bands extending right into the blue sensitive spectral region therefore give rise to a yellow discolouration of the finished image and reduced blue sensitivity in the recording material. Attempts have been made to solve this problem by introducing the UV absorbent in a highly divided form in a so called loadable latex, see Nos. DE-A 2,541,230 and 2,541,274. This process increases the absorption of the UV absorber at shorter wavelengths but the process is unsatisfactory.

It is also known to introduce photographically useful compounds in the form of polymers into recording materials. The use of polymeric UV absorbers has been disclosed in Nos. DE-A 3,313,574 and 3,327,464, U.S. Pat. No. 4,307,184 and DE-A 3,401,455. The use of polymerised anti-fogging agents has been disclosed in No. DE-A 3,341,352. The use of polymeric couplers has been disclosed, for example, in No. DE-A 3,401,455, DE-A 3,331,743 and DE-A 3,148,125 and U.S. Pat. No. 4,435,503.

Introducing the additives in this form still fails to meet all the requirements. The polymers disclosed in U.S. Pat. No. 4,307,184, for example, are either water soluble products which reduce the strength of the film due to excessive swelling or water insoluble, solid products which require to be emulsified by elaborate processes and the very large quantity of emulsifier generally necessary for this process results in the layer being excessively charged with emulsifier. Large quantities of emulsifier not only overload the layer but have other undesirable consequences such as inadequate sharpness, foaming during processing, loss of breaking strength and bleeding during storage.

It is an underlying aim of the present invention to provide an improved photographic recording material with stabilizing additives which does not have these disadvantages.

A photographic recording material having at least one light sensitive silver halide emulsion layer, optionally other layers and at least one stabilizer present in polymeric form has now been found. According to the invention, the stabilizer has recurrent structural units corresponding to the following formula (I)

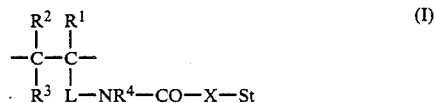

wherein
$R^1$, $R^3$ and $R^4$, which may be identical or different, denote H or alkyl with 1-4 carbon atoms,
$R^2$ which may be identical or different, denote H or alkyl with 1-4 carbon atoms or $COOR^1$,
L denotes a chemical bond or a divalent linking member,
X denotes 0 or $NR^4$, and St denotes a stabilizer or a group containing a stabilizer.

Stabilizers are understood for the purpose of the present invention to be compounds which stabilize the properties of the recording material, in particular stabilizers against the damaging effects of visible light, UV light heat and moisture also, formalin scavengers, stabilizers and anti-fogging agents for suppressing fog, and optical brightening agents.

In a preferred embodiment, $R^1$, $R^2$ and $R^4$ and optionally also $R^3$ are hydrogen.

In a preferred embodiment,
L denotes a chemical bond or the group -$L^1$—$L^2$/—, $L^1$, denotes —$CONR^1$/—, —$NR^1CO$—, CO—, —COO—, —$SO_2$, —COO—, —$SO_2$, —O— or a chemical bond, and $L^2$ denotes an optionally substituted alkylene group having 1 to 8 carbon atoms, an optionally substituted arylene group or a chemical bond.

In a particularly preferred embodiment, the group St is a unit which absorbs UV light.

The following, in particular, are suitable UV-light absorbent structures; aminoallylidene-malonitrile derivatives, hydroxy phenyl-benzotriazole derivatives, benzophenone derivatives, benzaldehyde derivatives, substituted acrylic acid derivatives, thiazolidone derivatives, α-and γ-benzopyrone derivatives, benzothiaiiazole derivatives, arylidene fluorenes and heterocyclic azines.

Stilbene compounds, coumarine derivatives, 1,3-diphenylpyrazoline derivatives, naphthalimide derivatives and benzoxazole derivatives are examples of suitable optical brightening agents.

The following are particularly suitable stabilizers against the damaging effects of visible light, heat and moisture; alkylated monophenols, alkylated hydroquinones and hydroquinone ethers, hydroxylated thiodiphenyl ethers, alkylidene-bisphenols, benzyl compounds, acylaminophenols, esters of β-(3,5-di-tertiary butyl-4-hydroxy phenyl)propionic acid and a monovalent or polyvalent alcohol, esters of β-(5-tertiary butyl-4-hydroxy-3-methylphenyl)propionic acid and a monovalent or polyvalent alcohol, amides of β-(3,5-di-tertiary butyl-4-hydroxyphenyl)propionic acid, esters of optionally substituted benzoic acids, nickel compounds, sterically hindered amines, oxalic acid diamides, phosphites and phosphonites and hydroxy chromans, hydroxy coumarins and their bisspiro compounds.

Suitable stabilizers for improving the resistance to formalin have been summarised in particular in U.S. Pat. No. 4,464,463.

Azaindenes, benzotriazoles, tetrazoles, acetylene derivatives and mercaptoazoles are particularly suitable stabilizers and anti-fogging agents for suppressing the silver halide fog.

The following are particularly preferred groups St:

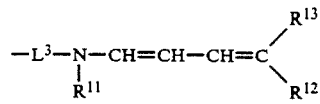 (1)

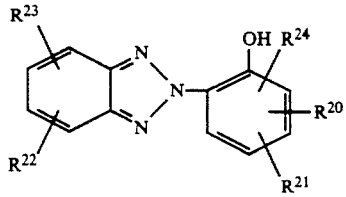 (2)

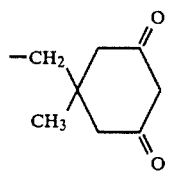 (3)

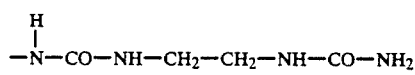 (4)

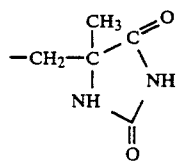 (5)

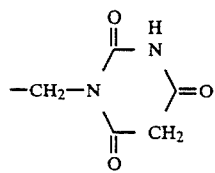 (6)

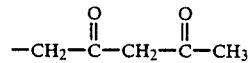 (7)

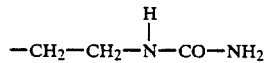 (8)

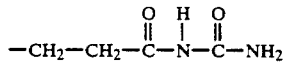 (9)

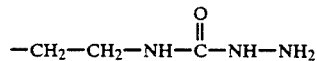 (10)

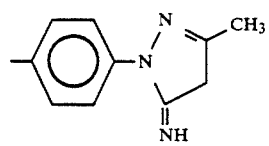 (11)

-continued

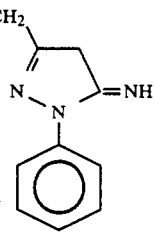 (12)

wherein $L^3$ denotes a linking group selected from an alkylene group having 1 to 20 carbon atoms (for example, a methylene group, an ethylene group, a trimethylene group, a 2-hydroxytrimethylene group, a pentamethylene group, a hexamethylene group, an ethylethylene group and a propylene group), $R^{11}$ denotes an alkyl group having 1 to 6 carbon atoms (e.g. methyl, ethyl, n-propyl, i-propyl, cyclohexyl), $R^{12}$ denotes a cyano group, $-COOR^{14}$, $-CONHR^{14}$, $-COR^{14}$ or $-SO_2R^{14}$, $R^{13}$ and denotes a cyano group, $COOR^{15}$, $CONHR^{15}$, $COR^{15}$ or $-SO_2R^{15}$ $R^{14}$ and $R^{15}$ which may be identical or different denote, for example, an optionally substituted alkyl group having 1 to 20 carbon atoms (for example, a methyl group, an ethyl group, a n-butyl group, a n-hexyl group, a cyclohexyl group, a n-decyl group, a n-dodecyl group, a n-octadecyl group, an eicosyl group, a methoxy ethyl group, an ethoxy propyl group, a 2-ethyl-hexyl group, a hydroxy ethyl group, a chloropropyl group, a N,N-diethylamino propyl group, a cyanoethyl group, a phenethyl group, a benzyl group, a p-tertiary butyl-phenethyl group, a p-tertiary octyl-phenoxy ethyl group, a 3-(2,4-di-tertiary-amyl-phenoxy)-propyl group, an ethoxy-carbonyl-methyl group, a 2-(2-hydroxyethoxy)-ethyl group, a 2-furyl-ethyl group, etc., or an aryl group with 6 to 20 carbon atoms (for example, a tolyl group, a phenyl group, an anisyl group, a mesityl group, a chlorophenyl group, a 2,4-di-tertiary-amyl-phenyl group, a naphthyl group, etc),in addition $R^{14}$ and $R^{15}$ may be joined together to form a 5- or 6-membered ring, for example a 1,3-dioxocyclohexane ring (e.g. a dimedorering, a 1,3-dioxo-5,5-diethyl-cyclohexane ring, etc), a 1,3-diaza-2,4,6-trioxo-cyclohexane ring (for example, a barbituric acid ring, a 1,3-dimethyl barbituric acid ring, a 1-phenyl-barbituric acid ring, a methyl-3-octyl-barbituric acid ring, a 1-ethyl-3-octyloxycarbonyl ethyl-barbituric acid ring, etc), a 1,2-diaza-3,5-dioxo-cyclopentane ring (for example, a 1,2-diaza-1,2-dimethyl-3,5-dioxo-cyclopentane ring, a 1,2-diaza-1,2-diphenyl-3,5-dioxocylcopentane ring, etc. or a 2,4-diaza-1-alkoxy-3,5-dioxo-cyclohexene ring (for example, a 2,4-diaza1-ethoxy-4-ethyl-3,5-dioxo-cyclohexene ring, a 2,4-diaza-1-ethoxy-4,3-(2,4-di-tertiary-amyl-phenoxy)-proply-3,5-dioxo-cyclohexene ring, etc.), and $R^{20}$ - $R^{24}$, which may be identical or different, denote H, halogen, $NO_2$, an alkyl or alkoxy group with 1 to 18 carbon atoms (optionally substituted), an aryl or aryloxy group (optionally substituted), or an amino group (optionally substituted).

One of the groups $R^{20}$–$R^{24}$ is a chemical bond or a divalent chemical linking member such as alkylene with 1 to 8 carbon atoms or arylene (optionally substituted). Compounds corresponding to the formula (I) which have the following structure are particularly preferred:

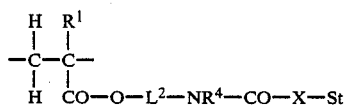 (II)

wherein
$R^1$ denotes H, or $CH_3$,
$R^4$ denotes H or $CH_3$,
$L^2$ denotes alkylene, in particular ethylene, butylene, or propylene, and
St has the meaning indicated above and is in particular a UV absorber
X denotes O or $NR^1$.

One particularly preferred type of UV absorber has the following structure:

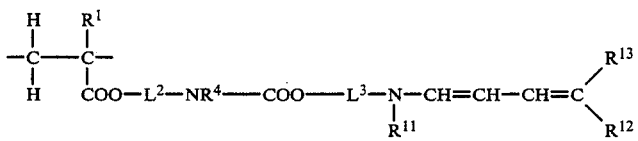 (III)

wherein the substituents have the following meanings:
$R^1$ denotes H, or $CH_3$,
$R^4$ denotes H, or $CH_3$,
$L^2$ and $L^3$, which may be identical or different, denote ethylene, propylene or butylene,
$R^{11}$ denotes an optionally substituted alkyl group, in particular one having 1–6 carbon atoms, denotes a cyano group or $-SO_2R^2R^{14}$,
$R^{13}$ denotes CN or $COOR^{15}$, and
$R^{14}/R^{15}$, which may be identical or different, denote an optionally substituted alkyl group having 1 to 20 carbon atoms, preferably 1 to 6 carbon atoms, or an optionally substituted aryl group having 6 to 20 carbonatoms.

In one particularly preferred embodiment, X in formulae I and II stands for oxygen.

Compounds having recurrent structural units corresponding to formula (I) may be prepared by conventional polymerisation of the corresponding starting monomers corresponding to the following formula (Ia)

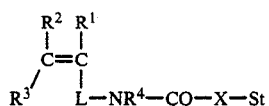 (Ia)

wherein the substituents have the meanings indicated for formula I.

Such monomers may be prepared by the reaction of stabilizers containing hydrox or amino groups with ethylenically unsaturated isocyanates.

Preparapion of the monomer M 1

36 g of 3-(N-rethyl-N-2-hydroxyethylamino-allylidene malonitrile and 31 g of isocyanato ethyl methacrylate in 250 ml of ethyl acetate are stirred for 3 hours at 25°–30° C. with the addition of 1 g of 1,4-diaza-bicyclo[2,2,2]octane and 0.5 g of ionol (2,6-di-tertiary butyl-4-methylphenol) and then left to stand over night. The solution is concentrated by evaporation under vacuum and the yellowish residue is dissolved in 70 ml of methanol at 30° C. with the addition of 0.5 g of ionol and then cooled to 0° C. The precipitate is filtered off and dried under vacuum at room temperature. 34 g of a yellowish product with a melting point of 73°–74° C. are obtained.

The following monomers are particularly preferred:

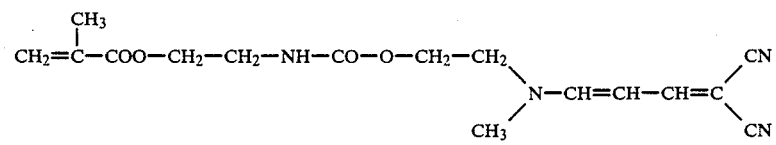 M 1

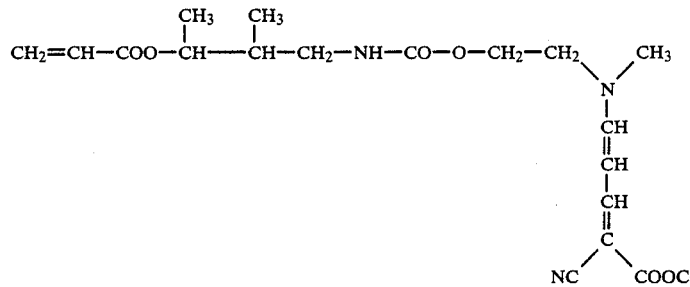 M 2

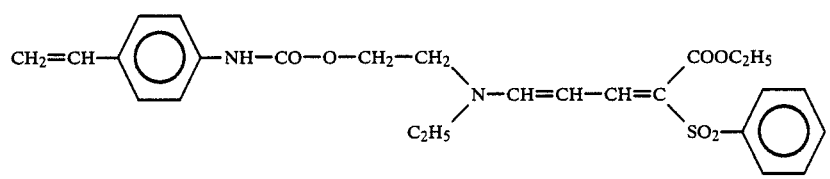 M 3

-continued
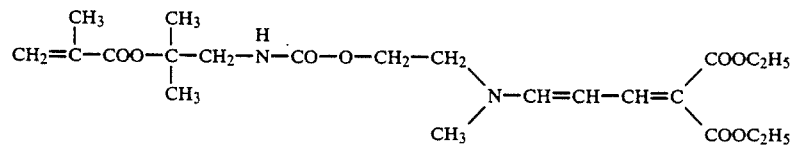
M 4
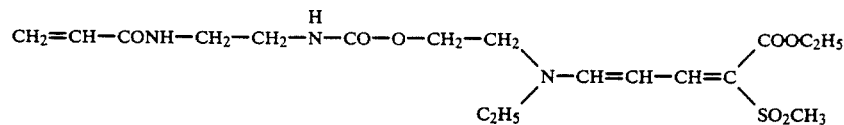
M 5
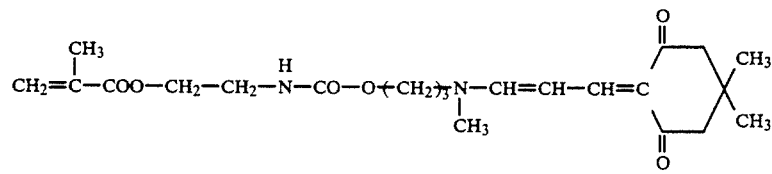
M 6
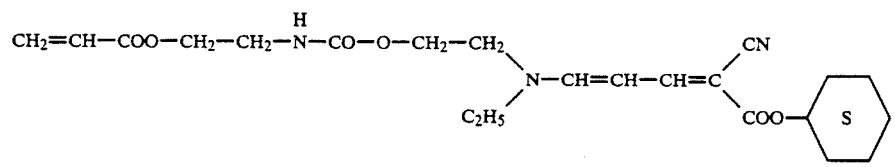
M 7
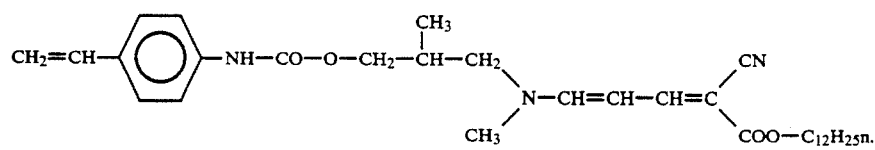
M 8
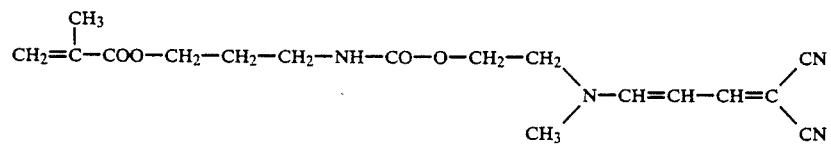
M 9
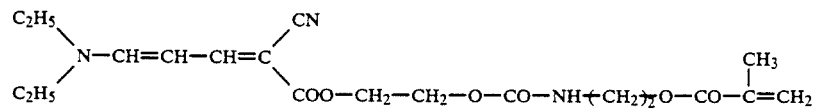
M 10
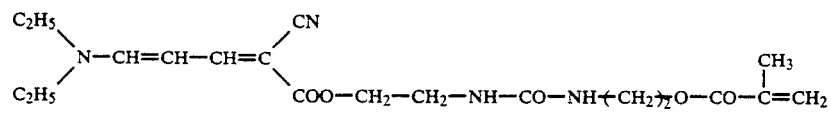
M 11
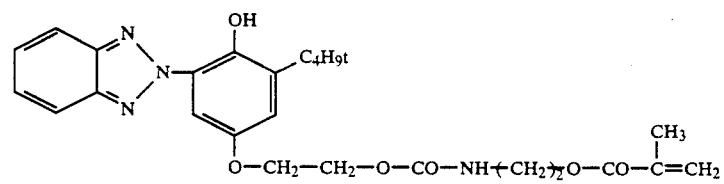
M 12
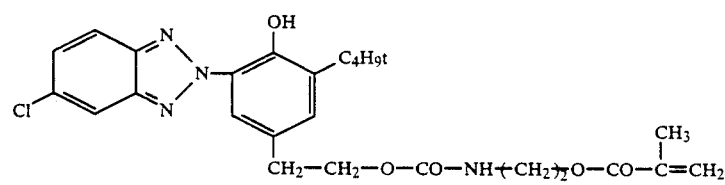
M 13

-continued
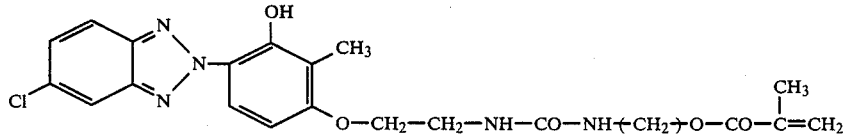
M 14
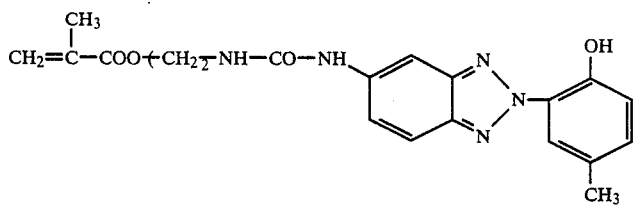
M 15
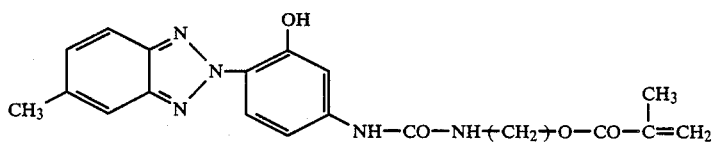
M 16
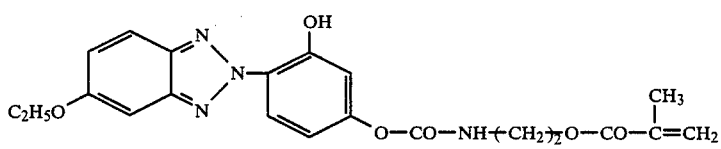
M 17
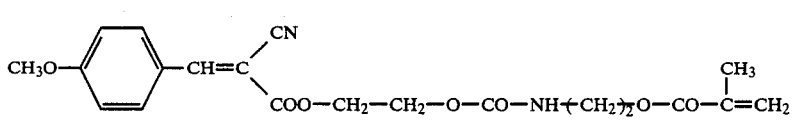
M 18
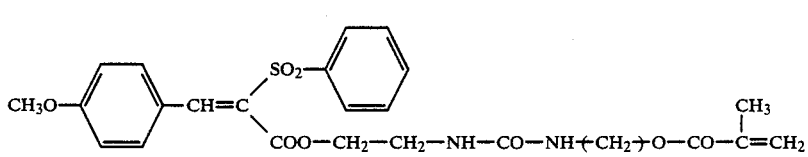
M 19
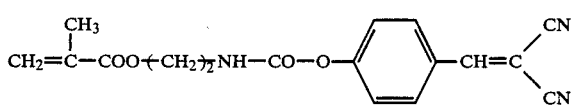
M 20
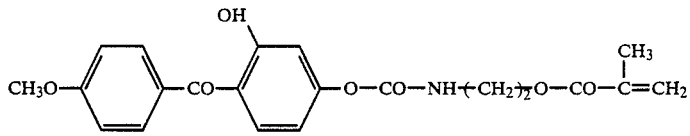
M 21
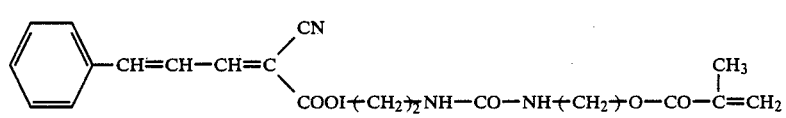
M 22
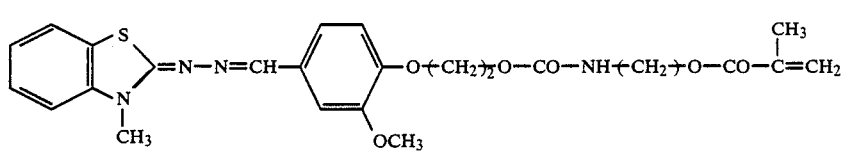
M 23
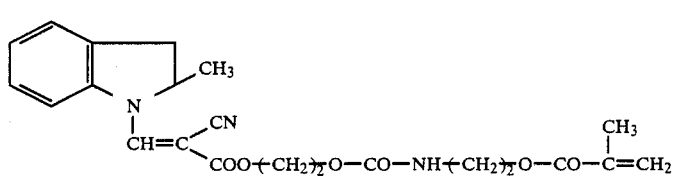
M 24

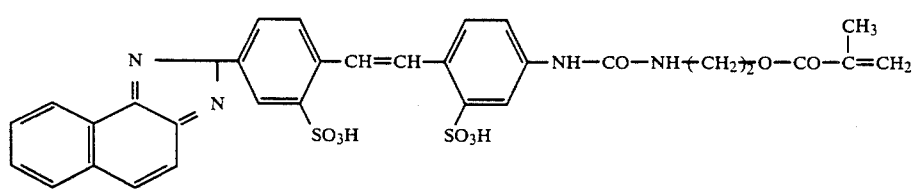
M 25
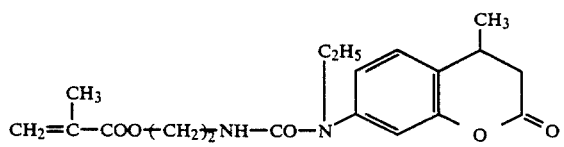
M 26
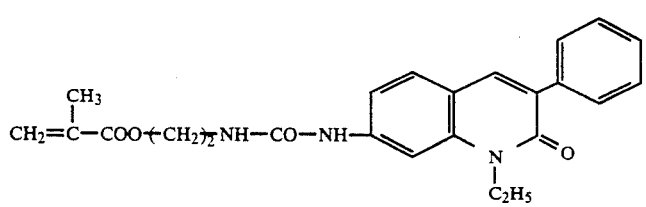
M 27
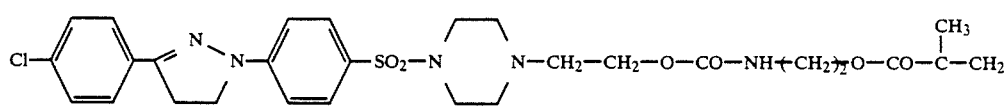
M 28
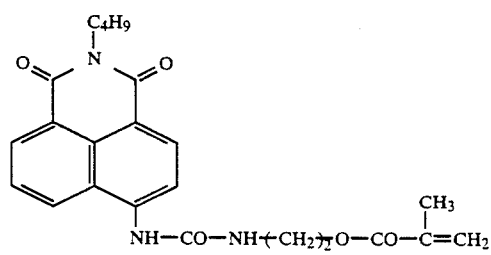
M 29
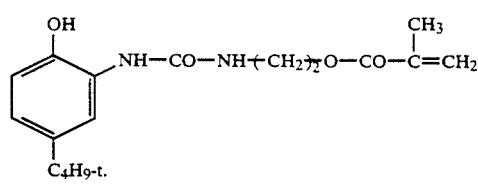
M 30
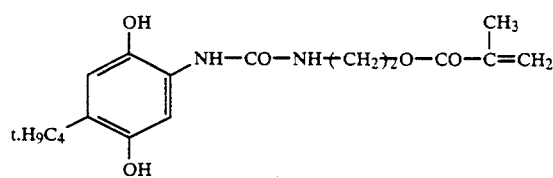
M 31
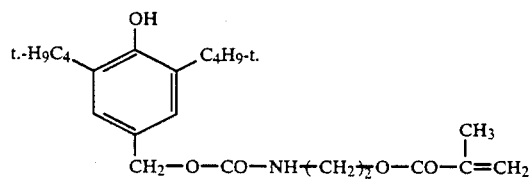
M 32

-continued

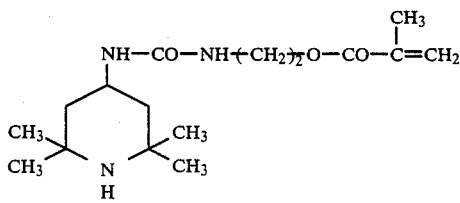
M 33

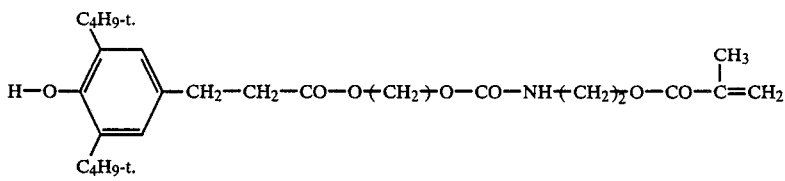
M 34

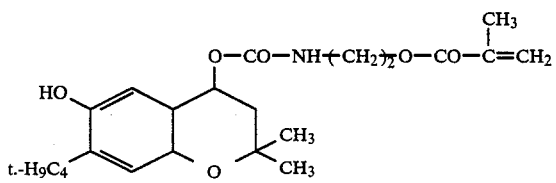
M 35

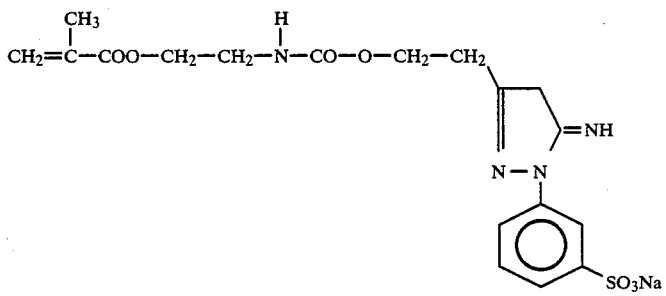
M 36

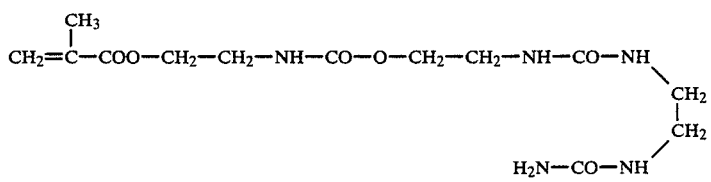
M 37

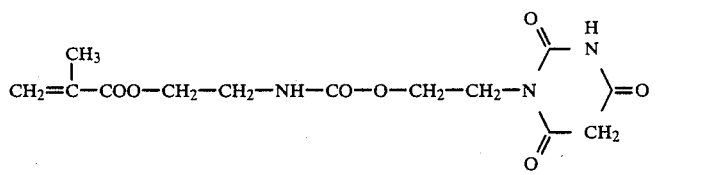
M 38

Other monomers may be used for polymerisation in addition to the starting monomers M so that copolymers are obtained.

Examples of momomers (comonomers) used for copolymerisation with th e monomers according to formula Ia include a ester preferably a lower alkyl ester and an amide derived from an acrylic acid, for example from acrylic acid itself, an α-chloroacrylic acid, an alkyl acrylic acid such as methacrylic acid, etc.(for example, acrylamide, methyl methacrylate, ethyl acrylate, ethyl methacrylate, n-propyl acrylate, n-butyl acrylate, 2-ethyl hexyl acrylate, n-hexyl acrylate, octyl methacrylate, lauryl methacrylate, methylene-bis-acrylamide, etc., a vinyl ester (for example, vinyl acetate, vinyl propionate, vinyl laurate, etc., acrylonitrile, methacrylonitrile, an aromatic vinyl compound (for example, styrene or a derivative thereof such as vinyl toluene, divinyl benzene, vinyl acetophenone, sulphostyrene, styrene sulphonic acid, etc.), itaconic acid, citraconic acid, crotonic acid, vinylidene chloride, a vinyl alkyl ether (for example, vinyl ethyl ether, etc., an ester of maleic acid, N-vinyl-2-pyrrolidone, N-vinyl pyridine, 2- and 4-vinyl pyridine, etc.

The molecular weights of the compounds according to the invention are preferably higher than 5,000, in particular higher than 20,000 in order to ensure sufficient resistance to diffusion. The upper limit is not critical and may reach values above 10 million, especially when the comonomers are bifunctional or poly-functional monomers.

It is particularly preferred if the monomers used include an ester of acrylic acid, an ester of methacrylic acid and an aromatic vinyl compound.

Two or more of the above described comonomer compounds may be used together. For example, there may be used a combination of n-butyl acrylate and divinyl benzene, styrene and methyl methacrylate, methyl acrylate and methacrylic acid, etc.

The ethylenically unsaturated monomer used for copolymerisation with monomer according to formula Ia may be particularly selected to exert and advantageous influence on the physical properties and/or chemical properties of the copolymer to be prepared, such as, for example, its solubility, its compatibility with a binder such as gelatine in the photographic colloid composition or with other photographic additives such as known photographic ultraviolet light absorbers known photographic antioxidants and known agents for producing the colour image, or the flexibility or thermal stability, etc.

In a preferred embodiment, the polymers according to the invention are used as a polymer dispersion or as a polyxer latex.

The polymer latex according to the invention may be prepared by a process of emulsion polymerisation or by the polymerisation of a monomer in an organic solvent followed by dispersion of the solution in latex form in an aqueous solution of gelatine.

The free radical polymerisation of an ethylenically unsaturated monomer is initiated by the addition of a free radical which is formed by thermal decomposition of a chemical initiator, by the action of a reducing agent on an oxidizing compound (Redox initiator) or by a physical action such as irradiation with ultraviolet light or other high energy rays, high frequency, etc.

Examples of primarily chemical initiators include persulphates (for example, ammonium persulphate or potassium persulphate, eto), hydrogen peroxides, peroxides (such as benzoyl peroxide or tertiary butyl perocto-ate, etc.) and azonitrile compounds (for example, 4,4'-azo-bis-4-cyanovaleric acid, azo-bis-isobutyronitrile, etc.), and so forth.

Examples of conventional Redox initiators include the systems hydrogen peroxide-iron (II) salts; potassium persulphate-sodium metabisulphite and cerium (IV) salt-alcohol, etc.

Examples of initiators and their functions are described by F.A. Bovey in Emulsion Polymerisation, Interscience Publishers Inc., New York, 1955, pages 59 to 93.

The emulsifier used for emulsion polymerisation may be a compound having surface active properties. Preferred examples of such emulsifiers include soaps, sulphonates, sulphates, cationic compounds, amphoteric compounds and high molecular weight protective colloids Specific examples of emulsifiers and their functions are described in Belgische Chemische Industrie, Volume 28, pages 16 to 20, 1963.

One special advantage of the compounds to be used according to the invention is that they require only small quantities of emulsifier for emulsion polymerisation. In a preferred embodiment, a maximum of 8%, in particular a maximum of only 6% of emulsifiuer is used, based on the quantity of polymer.

In another form of application, the polymer is dispersed. When the polymer corresponding to formula (I) is dispersed in an aqueous gelatine solution in latex form, organic solvent used for dissolving may be removed from the mixture before the coating is formed from the dispersion.

The solvents used may be to some extent soluble in water so that they can be removed by washing with water when the gelatine is in the form of noodles or they may be of the kind which can be removed by spray drying or vacuum or vapour rinsing.

The examples of suitable organic solvents capable of being removed include esters (for example, lower alkyl esters, etc.), lower alkyl ethers, ketones, halogenated hydrocarbons (for example, methylene chloride, trichloroethylene, etc.), fluorinated hydrocarbons, alcohols (for example, methyl- to butyl-alcohols) and a combination thereof.

Any type of dispersing agent may be used for dispersing compounds according to the invention although ionic surface active agents and particularly anionic surface active agents are preferred.

Ampholytic surface active agents such as C-cetyl betaine, N-alkyl-aminopropionates, N-alkyl-imino dipropionate etc. may also be used.

A small quantity (not more than 50% by weight of the recurrent units of formula (I)) of a permanent solvent, namely an organic solvent with a high boiling point (i.e. above 200° C.) which is immiscible with water, e.g. dibutyl phthalate and/or tricresyl phosphate, etc. may be added to improve the stability of dispersion and the flexibility of the emulsion. The concentration of the permanent solvent must be sufficiently low to plasticize the polymer while the latter is kept in a state of solid particles. Furthermore, if a permanent solvent is used, it should be present in as small a quantity as possible so that the emulsion layer or hydrophilic colloid layer ultimately obtained may be as thin as possible for the sake of sharpness of the image.

The compounds to be used according to the invention may be introduced, for example, into a layer of binder or a light sensitive silver halide emulsion layer, depending on the nature of the group St. If St is a structure protecting against UV light and visible light, the compound is preferably introduced into an upper layer, e.g. a layer situated above all the light sensitive layers.

If St is a structure suppressing fogging, the compound is preferably introduced into a silver halide emulsion layer.

The quantity to be used depends upon the particular purpose for which the compound is required, and can easily be optimized in the usual manner. The following are examples of preferred quantities:

When used as protection against UV and visible light: 50–1000 mg/m$^2$.

When used as formalin scavenger: 100–2000 mg/m$^2$, in particular 0.5–12 mol per mol of magenta 4-equivalent coupler.

When used as stabilizer or anti-fogging agent against silver halide fog: 10–300 mg per 100 g of silver, calculated as AgNO$_3$.

Apart from the layers already mentioned above, the colour photographic recording material according to the invention may contain other, light insensitive auxiliary layers, e.g. bonding layers, antihalation layers or covering layers, in particular inter layers between the light sensitive layers to prevent the diffusion of developer oxidation products from one layer into another layer.

The light sensitive silver halide emulsion layers may be split up into partial layers having differing sensitivities.

Colour couplers capable of reacting with the colour developer oxidation products to form non-diffusible dyes are associated with the light sensitive silver halide emulsion layers. The colour couplers are advantageously accommodated in a non-diffusible form in the light sensitive layer itself or closely adjacent thereto.

Thus the red sensitive layer, for example, may contain a non-diffusible colour coupler to produce the cyan partial colour image, generally a coupler of the L phenol or α-naphthol series. The green sensitive layer, for example, may contain at least one non-diffusible colour coupler to produce the magenta partial colour image, usual a colour coupler of the 5-pyrazolone series. The blue sensitive layer, for example, may contain at least one non-diffusible colour coupler to produce the yellow partial colour image, generally a colour coupler having an open chain keto-methylene group. The colour couplers may be, for example, 6-, 4- or 2-equivalent couplers. Suitable couplers have been disclosed, for example, in the publications "Farbkuppler" by W. Pelz in "Mitteilungen aus den Forschungslaboratorien der Agfa, Leverkusen/Munchen", Volume III, page 111 (1961); K. Venkataraman in "The Chemistry of Synthetic Dyes", Volume 4, 341 to 387, Academic Press ( 1971) and T.H. James, "The Theory of the Photographic Process", 4th Edition, pages 353–362, and the Journal "Research Disclosure" , No. 17643 of December 1978, Section VII, published by Industiral Opportunities Ltd., Homewell Havant, Hampshire, PO9 1 EF, Great Britain.

The recording material may also contain DIR compounds and white couplers which do not form a dye when they react with colour developer oxidation products. The inhibitors may be split off from the DIR compounds either directly or by way of non-inhibitory intermediate compounds. See No. GB 953,454, U.S. Pat. Nos. 3,632,345, 4,248,962 and No. GB 2,072,363.

The halides contained in the light sensitive silver halide emulsions used may be chloride, bromide, iodide or mixtures thereof. In a preferred embodiment, the halide content of at least one layer is composed of 0–12 mol % of AgI, 0 to 50 mol % of AgCl and 50 to 100% of AgBr, the percentages adding up to 100%.

In a preferred embodiment, the silver halides consist predominantly of compact crystals which may be, for example, cubic or octahedral or transitional forms. They may be characterised by their thickness which is mainly greater than 0.2 μm. The average ratio of diameter to thickness is preferably less than 8:1, the diameter of a grain being defined as the diameter of a circle having an area equal to the projected area of the grain.

In another preferred embodiment, either the whole emulsion or individual portions of the emulsion may consist substantially of tabular silver halide crystals in which the ratio of diameter to thickness is greater than 8:1.

The emulsions may be chemically sensitized. The usual sensitizers for silver halide grains may be used for this purpose, compounds containing sulphur, such as allyl isothiocyanate, allylthiourea and thiosulphates being particularly preferred.

Noble metals such as gold, platinum, palladium, iridium, ruthenium or rhodium and compounds of these metals are also suitable chemical sensitizers. This method of chemical sensitization has been described in the article by R. Koslowsky, Z. Wiss. Phot. 46, 65–72 (1951). The emulsions may also be sensitized with polyalkylene oxide derivatives. See also the above mentioned Research Disclosure No. 17,643, section III.

The emulsions may be optically sensitized in a known manner, e.g. by means of the usual polymethine dyes such as neutrocyanines, basic or acid carbocyanines, rhodacyanines, hemicyanines, styryl dyes, oxonoles and the like. Sensitizers of this kind have been described by F.M. Hamer in "The Cyanine Dyes and related compounds", (1964). See also in particular Ullmanns Enzyklopadie der technischen Chemie, 4th Edition, Volume 18, pages 431 et seq, and the above mentioned Research Disclosure No. 17643, Section IV.

The usual anti-fogging agents and stabilizers may be used in addition to the compounds used according to the invention. Azaindenes are particularly suitable stabilizers, especially tetra and penta-azaindenes and more particularly those which are substituted with hydroxyl or amino groups Such compounds have been described e.g. in the article by Birr, Z. Wiss, Phot. 47, (1952) pages 2–58. Other suitable stabilizers and anti-fogging agents are given in the above mentioned Research Disclosure No. 17643, in Section IV.

The components of the photographic material may be incorporated by conventional, known methods. Compounds which are soluble in water or alkalis may be added in the form of aqueous solutions, optionally with the addition of water miscible organic solvents such as ethanol, acetone or dimethyl formamide. Compounds which are insoluble in water or alkalis may be incorporated in the recording materials in the form of dispersions in aknown manner. For example, a solution of such compounds in a low boiling organic solvent may be mixed directly with the silver halide emulsion or it may first be mixed with an aqueous gelatine solution from which the organic solvent is then removed, and the resulting dispersion of the particular compound may then be mixed with the silver halide emulsion. So called oil formers are optionally used in addition. These are generally relatively high boiling organic compounds in which. the compounds to be dispersed are enclosed in the form of oily droplets. See in this connection, for example, U.S. Pat. Nos. 2,322,027; 2,533,514; 3,689,271; 3,764,336 and 3,765,897. It is also possible, for example, to incorporate couplers in the form of loaded latices, see No. DE-OS 2,541,274 and No. EP-A 14,921. The components may also be fixed in the material as polymers, see e.g. No. DE-OS 2,044,992, U.S. Pat. No. 3,370,952 and U.S. Pat. No. 4,080,211.

The usual layer supports may be used for the materials according to the invention, e.g. supports of cellulose esters such as cellulose acetate or of polyesters. Paper supports are also suitable, and these may be coated, e.g. with polyolefins, in particular with polyethylene or polypropylene. See in this connection the above mentioned Research Disclosure No. 17643, Section XVII.

The usual hydrophilic film forming agents may be used as protective colloids or binders for the layers of recording material, e.g. proteins, in particular gelatine. See the binders indicated in the above mentioned Research Disclosure No. 17643, Section IX.

The layers of photographic material may be hardened in the usual manner, for example with epoxide type hardeners or hardeners of the heterocyclic ethylene imine or acryloyl type. The layers may also be hardened by the process according to German Offenlegungsschrift No. 2,218,009 to produce colour photographic materials suitable for high temperature processing. Furthermore, the photographic layers or colour photographic multi-layered materials may be hardened with hardeners of the diazine, triazine or 1,2-dihydroquinoline series or with vinyl sulphone type hardeners. Other suitable hardeners are disclosed in German Offenlegungsschriften No. 2,439,551, 2,225,230 and 2,317,672 and in the above mentioned Research Disclosure No. 17643, Section XI.

Other suitable additives are given in Research Disclosure 17643 and in "Product Licensing Index" of December 1971, pages 107–110.

Suitable colour developer substances for the material according to the invention include in particular those of the p-phenylene diamine series, e.g. 4-amino-N,N-diethyl-aniline hydrochloride; 4-amino-3-methyl-N-ethyl-N-β-(methanesulphonamido)-ethyl aniline sulphate hydrate; 4-amino-3-methyl-N-ethyl-N-β-hydroxyethyl aniline sulphate; 4-amino-N-ethyl-N-(2-methoxyethyl)-m-toluidine-di-p-toluene sulphonic acid and N-ethyl-N-β-hydroxyethyl-pphenylene diamine. Other suitable colour developers have been described, for example, in J. Amer. Chem. Soc. 73, 3100 (1951) and in G. Haist, Modern Photographic Processing, 1979, John Wiley and Sons, New York, pages 545 et seq.

After colour development, the material is bleached and fixed in the usual manner. Bleaching and fixing may be carried out separately or together The usual bleaching agents may be used, e.g. $Fe^{3+}$ salts and $Fe3+$ complex salts such as ferricyanides, dichromates, water soluble cobalt complexes etc. Iron-III complexes of aminopolycarboxylic acids are particularly preferred, in particular e.g. ethylene diamino tetraacetic acid, nitrilotiacetic acid, imino-diacetic acid, N-hydroxyethylethylene diamino-triacetic acid, alkyl iminodicarboxylic acids and corresponding phosphonic acids. Persulphates are also suitable bleaching agents.

EXAMPLES

The compounds mentioned in the following examples have the structures shown below:
Uv-1 (comparison)

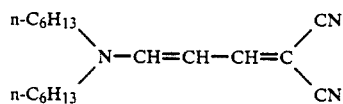

UV-2 (comparison)
Compound according to Example 1 of U.S. Pat. No. 4,307,184 (acrylamide-diallylamino-allylidene malonitrile copolymer)
UV-3 (invention)

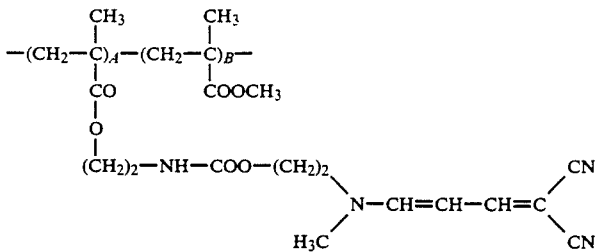

Froportions by weight: A,50%, B,50%.
Uv-4 (invention)

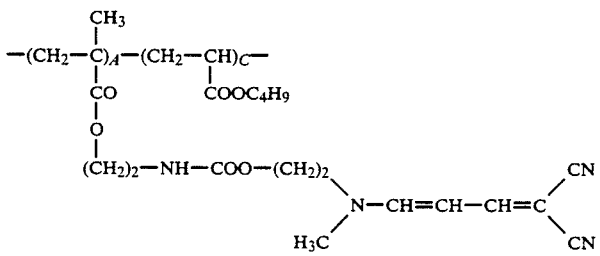

Proportions by weight: A =50%, C=50%

Compounds UV-3 and UV-4 according to the invention were prepared as follows:

Polymer latex UV-3

0.8 g of a 50% solution of sodium dodecyl diphenyl ether disulphate and 50 ml of water were heated to 70° C. under nitrogen 2.5 g of a mixture of 10 g of monomer compound M 1 and 10 g of methyl methacrylate were then added and a solution of 0.1 g of potassium peroxydisulphate in 5 ml of water and 0.1 g of sodium metabisulphite in 5ml of water was introduced dropwise. The remaining quantity of monomer mixture was added dropwise after 10 minutes at 70° C. A finely divided latex having a solids content of 21.8% was obtained after 3 hours stirring at 70° C.

Polymer latex UV-4

0.8 g of a 50% solution of sodium dodecyl diphenyl ether disulphate and 50 ml of water were heated together to 70° C. under nitrogen 2.5 g of a mixture of 10 g of monomer compound M 1 and 10 g of butyl acrylate were added. A solution of 0.1 g of potassium peroxydisulphate in 5 ml of water and 0.1 g of sodium metabisulphite in 5 ml of water was then introduced dropwise and the remaining quantity of monomer mixture was added dropwise after 10 minutes. A finely divided latex having a solids content of 22.2% was obtained after 3 hours.

EXAMPLE 1

A casting solution containing a UV absorber, gelatine and sodium dodecylbenzene sulphonate was cast on a triacetate support in the usual manner. The quantity was adjusted to provide 0.2 m mol of the given UV chromophore per m². The gelatine concentration was adjusted to provide 1 g of gelatine per m². Over this UV absorber layer was applied a pure gelatine layer containing 1 g of gelatine per m². Dispersions of the UV absorbers were first prepared by taking up the compounds in ethyl acetate and then mixing with gelatine with the aid of a high speed stirrer and subsequently homogenizing in a high pressure homogenizer. The films prepared by this method were examined in a spectrometer, using a film free from UV absorber as reference The UV spectra shown in FIG. 1 were obtained. The curves in FIG. 1 have the following meanings:

Curve 1: material containing UV absorber UV-1
Curve. 2: UV absorber UV-2
Curve 3: UV absorber UV-3
Curve 4: UV absorber UV-4

It is obvious that the UV absorbers UV-3 and UV-4 according to the invention show better absorption.

EXAMPLE 2

A conventional colour photographic negative material was obtained by applying the following layers in the given sequence to a conventional support:

A low sensitivity red sensitive layer r
A high sensitivity red sensitive layer R
A low sensitivity green sensitive layer g
A high sensitivity green sensitive layer G
A yellow filter layer of colloidal silver filter yellow
A low sensitivity blue sensitive layer b
A high sensitivity blue sensitive layer B
UV- layer according to Example 1
Gelatine layer according to Example 1.

The samples were exposed imagewise and subjected to a conventional process of colour negative development, for example as disclosed in No. DE-A 3,029,209. The following results were obtained, compared with those of a sample containing no UV absorber:

| Sample | UV absorber | Blue sensitive layers | | Brown reproduction |
| | | reduction in sensitivity | Increase in $D_{min}$ | |
|---|---|---|---|---|
| 1 | UV-1 | 0.16 lg(Ixt) | 0.06 | Brown |
| 2 | UV-2 | 0.07 lg(Ixt) | 0.01 | Dirty violet |
| 3 | UV-3 | 0.11 lg(Ixt) | 0.01 | Brown |
| 4 | UV-4 | 0.10 lg(Ixt) | 0.01 | Brown |

Reduction in sensitivity:
An increase in sensitivity in terms of lg (Ixt) by 0.3 units corresponds to a doubling in sensitivity.
$D_{min}$: minimum colour density
Brown reproduction:
A brown object colour with strong remission in the long wave UV range was photographed. The reproduction was assessed by reference to a neutral copy.

The Table shows that samples 3 and 4 according to the invention provide an improvement in sensitvity compared with Sample 1 and improved colour reproduction compared with Sample 2.

We claim:

1. Fhotographic recording material having at least one light sensitive silver halide emulsion layer, and at least one UV-stabilizer present in a polymeric form, in an amount of 50 to 1000 mg/m$^2$ of recording material, characterized in that the Uv-stabilizer has recurrent structural units corresponding to the following formula

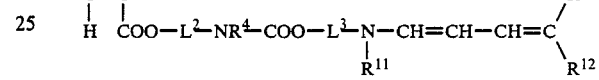

wherein
$R^1$ denotes H or CH$_3$
$R^4$ denotes H or CH$_3$,
$L^2$ and $L^3$, which may be identical or different, denote ethylene, propylene or butylene,
$R^{11}$ denotes an unsubstituted or substituted alkyl group,
$R^{12}$ denotes a cyano group or -SO$_2$R$^{14}$,
$R^{13}$ denotes CN or COOR$^{15}$, and
$R^{14}$/$R^{15}$, which may be identical or different, denote an unsubstituted or substituted alkyl group having 1–20 carbon atoms or an unsubstituted or substituted aryl group having 6–20 carbon atoms.

2. Material according to claim 1, characterised in that the UV-absorber is arranged above the light sensitive silver halide emulsion layers.

* * * * *